United States Patent
Hung et al.

(10) Patent No.: US 9,603,571 B2
(45) Date of Patent: Mar. 28, 2017

(54) WEARABLE ELECTROCARDIOGRAM MEASUREMENT DEVICE AND METHOD FOR COMPRESSING AN ELECTROCARDIOGRAM

(71) Applicant: NATIONAL KAOHSIUNG FIRST UNIVERSITY OF SCIENCE AND TECHNOLOGY, Kaohsiung (TW)

(72) Inventors: King-Chu Hung, Taoyuan (TW); Huan-Sheng Wang, New Taipei (TW); Jui-Hung Hsieh, Tainan (TW); Je-Hung Liu, Tainan (TW); Pei-Jen Chang, Kaohsiung (TW)

(73) Assignee: National Kaohsiung First University of Science and Technology, Kaohsiung (TW)

( * ) Notice: Subject to any disclaimer, the term of this patent is extended or adjusted under 35 U.S.C. 154(b) by 16 days.

(21) Appl. No.: 14/840,253

(22) Filed: Aug. 31, 2015

(65) Prior Publication Data

US 2017/0055914 A1    Mar. 2, 2017

(51) Int. Cl.

| | | |
|---|---|---|
| *A61B 5/0402* | (2006.01) | |
| *A61B 5/00* | (2006.01) | |
| *A61B 5/0432* | (2006.01) | |
| *A61B 5/0408* | (2006.01) | |
| *A61B 5/04* | (2006.01) | |

(52) U.S. Cl.
CPC .......... *A61B 5/7232* (2013.01); *A61B 5/0006* (2013.01); *A61B 5/0022* (2013.01); *A61B 5/0408* (2013.01); *A61B 5/04017* (2013.01); *A61B 5/0432* (2013.01)

(58) Field of Classification Search
CPC ................................. A61B 5/04; A61B 5/0402
USPC ........................................................ 600/509
See application file for complete search history.

(56) References Cited

U.S. PATENT DOCUMENTS

| 9,326,734 B1 * | 5/2016 | Chai ..................... A61B 5/7232 |
| 2008/0177789 A1 * | 7/2008 | Stoval .................. A61B 5/0002 |

* cited by examiner

*Primary Examiner* — Carl H Layno
*Assistant Examiner* — Jon Eric C Morales
(74) *Attorney, Agent, or Firm* — Rosenberg, Klein & Lee

(57) ABSTRACT

A wearable electrocardiogram measurement device and a method for compressing an electrocardiogram are disclosed. A heart detection unit detects a heart activity status of a human body to obtain electrocardiogram data. A processor of a portable host proceeds with bandwidth decomposition and quantization by using quantization scales to obtain quantized results. An integer part of each quantized result is set as a quantized datum. A decimal portion of each quantized result is set as a truncated error datum. Each quantization scale is multiplied by a corresponding truncated error datum to obtain a product. If a distortion value obtained by adding the products fulfills a distortion default value range, the quantized data are encoded to obtain compressed electrocardiogram data for storage in a data storage unit of the host. If the distortion value does not fulfill the distortion default value range, an adjustment step is repeated.

7 Claims, 3 Drawing Sheets

WEARABLE ELECTROCARDIOGRAM MEASUREMENT DEVICE AND METHOD FOR COMPRESSING AN ELECTROCARDIOGRAM

BACKGROUND OF THE INVENTION

The present invention relates to a measurement device and a data compressing method and, more particularly, to a wearable electrocardiogram measurement device and a method for compressing an electrocardiogram.

The heart is the most important and the most complicated organ among the human organs. With the development of technology, the operation and beating of the heart can be observed through instruments to judge whether abnormal heart conditions occur. An electrocardiogram (ECG) obtained by measuring the heart beating is one of the major judgement bases. To accurately capture the heart activity status, a 12-lead system (namely, 12-lead ECG) utilizes 12 leads on the front side and the horizontal plane to record the electrophysical activity of the heart from 12 different directions, obtaining 12 electrocardiogram data. Thus, a doctor can observe the operating pattern of the cardiac electrical pulses from 12 different angles to judge the heart activity status or to judge the causes of heart disease.

However, the electrocardiograms requires a long period of time of observation and recording plus measurement of the heart beating conditions from 12 different directions, the overall data is huge and occupies a considerable space of a hard disc. It is, thus, an important issue in preventing data distortion after compressing and decompressing while providing a better amount of compression. The value of the percentage root mean square difference (PRD) is the index of distortion and is preferably between 2% and 7%.

FIG. 3 is a diagrammatic block diagram illustrating a conventional method for compressing electrocardiogram data. A PRD value (the target value) is preset before the measurement. After the electrocardiogram data have undergone bandwidth decomposition, quantization, error control, and encoding, since the PRD value after decompression must fulfill the preset value, decoding analysis, inverse quantization, and inverse bandwidth decomposition must be conducted to compare the compressed data with the original data for judging whether the PRD is within 5% fluctuation range of the target value. After compression, since decoding analysis, inverse quantization, and inverse bandwidth decomposition must be carried out to permit comparison of the PRD value, the data compressing takes a long time and, thus, increases the burden to the processor. Furthermore, since obtaining the electrocardiogram data requires a considerable time for continuously observing the heart activity status, the patient must stay in the hospital for a long period of time, which is extremely inconvenient.

Thus, a need exists for a method for obtaining the electrocardiogram data without affecting the living of the patient. Furthermore, the PRD comparison can be proceeded while carrying out bandwidth decomposition, quantization, error control, and encoding. Thus, about half of the data compressing time can be saved to reduce the burden to the instrument.

BRIEF SUMMARY OF THE INVENTION

In an aspect, a wearable electrocardiogram measurement device includes a heart detection unit and a host. The heart detection unit is adapted to be mounted to a skin of a human body for detecting an activity status of a heart of the human body to obtain electrocardiogram data. The host is portable by a user and includes a data storage unit and a processor. The data storage unit is configured to store compressed electrocardiogram data. The processor is electrically connected to the heart detection unit and the data storage unit. First, second, and third electrocardiogram compressing programs and a distortion default value are written into the processor.

The first electrocardiogram compressing program is executable by the processor to proceed with bandwidth decomposition of sensed data obtained from the heart detection unit, obtaining a plurality of bandwidth data.

The second electrocardiogram compressing program is executable by the processor to proceed with quantization of the plurality of bandwidth data respectively by using a plurality of quantization scales to obtain a plurality of quantized results. An integer part of each of the plurality of quantized results is set as a quantized datum. A decimal portion of each of the plurality of quantized results is set as a truncated error datum. Each of the plurality of quantization scales is multiplied by a corresponding truncated error datum to obtain a product, and a distortion value is obtained by adding the products.

When the distortion value is not larger than the distortion default value or fulfills a distortion default value range, the third electrocardiogram compressing program is executed.

When the distortion value is larger than the distortion default value or does not fulfill the distortion default value range, a value represented by each of plurality of quantization scales is changed, and the second electrocardiogram compressing program is re-executed.

The third electrocardiogram compressing program is executable by the processor to encode the quantized data to obtain the compressed electrocardiogram data, and the compressed electrocardiogram data are sent to the data storage unit for storage.

The plurality of bandwidth data can include a first level bandwidth datum and a second level bandwidth datum. Data of a filter matrix can be written into the processor. The first electrocardiogram compressing program is executable by the processor to multiply the sensed data by the filter matrix to obtain the first level bandwidth datum and the second level bandwidth datum.

A quantization scale program can be written into the processor. The quantization scale program is executable by the processor. Each of the plurality of quantization scales corresponds to a quadratic equation with one unknown. A quantization scale factor is selected to obtain the plurality of quantization scales by using each quadratic equation with one unknown.

The host can further include an antenna unit permitting transmission of the compressed electrocardiogram data to a cloud server.

In a second aspect, a method for compressing an electrocardiogram includes:

(A) proceeding with bandwidth decomposition of electrocardiogram data to obtain a plurality of bandwidth data;

(B) using a plurality of quantization scales to proceed with respective quantization of the plurality of bandwidth data to obtain a plurality of quantized results, with an integer part of each of the plurality of quantized results being set as a quantized datum, with a decimal portion of each of the plurality of quantized results being set as a truncated error datum, and proceeding with an error control in which each of the plurality of quantization scales is multiplied by a corresponding truncated error datum to obtain a product, and a distortion value is obtained by adding the products, wherein when the distortion value is not larger than the distortion default value or fulfills a distortion default value range, a step (C) is executed, wherein when the distortion value is larger than the distortion default value or does not fulfill the distortion default value range, a value represented by each of plurality of quantization scales is changed, and the step (B) is re-executed; and encoding the quantized data to obtain compressed electrocardiogram data.

In the step (A), the plurality of bandwidth data can include a first level bandwidth datum and a second level bandwidth datum, and the electrocardiogram data is multiplied by a filter matrix to obtain the first level bandwidth datum and the second level bandwidth datum.

In the step (B), each of the plurality of quantization scales corresponds to a quadratic equation with one unknown, and a quantization scale factor is selected to obtain the plurality of quantization scales by using each quadratic equation with one unknown.

The present invention will become clearer in light of the following detailed description of illustrative embodiments of this invention described in connection with the drawings.

DETAILED DESCRIPTION OF THE INVENTION

Figure 1:
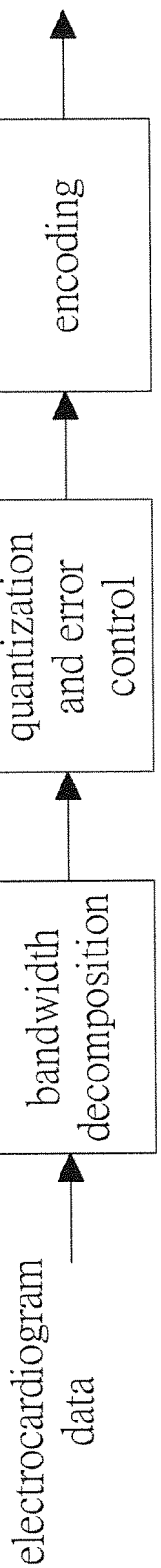
FIG. 1 is a diagrammatic block diagram illustrating a method for compressing an electrocardiogram according to the present invention.
Figure 2:
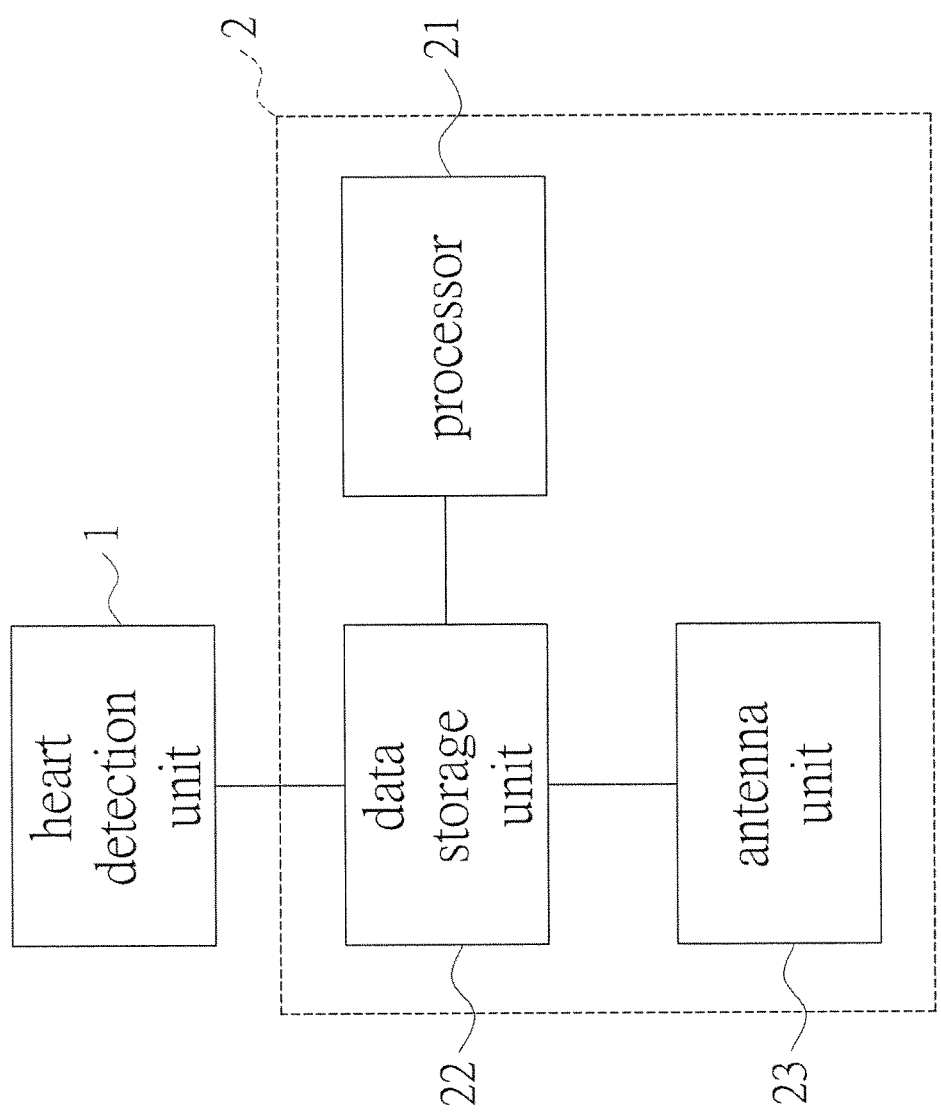
FIG. 2 is a diagrammatic block diagram illustrating the connection between elements of a wearable electrocardiogram measurement device according to the present invention.

With reference to FIGS. 1 and 2, a wearable electrocardiogram measurement device according to the present invention includes a heart detection unit 1. The heart detection unit 1 is adapted to be mounted to a skin of a human body for detecting an activity status of a heart of the human body to obtain electrocardiogram data. Since the heart includes left and right ventricles and left and right atria, to know the whole activity status of the heart, the heart detection unit 1 preferably includes 12 sub-detection units mounted to different portions of the human body, such as the arms, the ribs, etc., to observe the hear activity from different directions and different angles. The sensed results of the sub-detection units together form an electrocardiogram.

The wearable electrocardiogram measurement device further includes a host 2 portable by a user. The host 2 includes a data storage unit 21 and a processor 22. The data storage unit 21 is configured to store compressed electrocardiogram data. The processor 22 is electrically connected to the heart detection unit 1 and the data storage unit 21. A distortion default value and first, second, and third electrocardiogram compressing programs are written into the processor 22. The distortion default value can be set by an input unit electrically connected to the processor 22 or can be a basic setting during manufacture of the host 2. Academically, the percentage root mean square difference (PRD) means the distortion of the electrocardiogram is within 5% fluctuation range of the preset value. Considering the distortion of the electrocardiogram and the storage capacity, the distortion default value is preferably between 2% and 7%.

The first, second, and third electrocardiogram compressing programs will now be set forth hereinafter.

Firstly, the first electrocardiogram compressing program is executable by the processor 22 to proceed with bandwidth decomposition. The decomposition uses integer arithmetic operation, such that the sensed data obtained from the heart detection unit 1 is decomposed to obtain a plurality of bandwidth data. The bandwidth data includes a first level bandwidth datum and a second level bandwidth datum. Note that the bandwidth data can include first to eleventh level bandwidth data to provide the electrocardiogram with better compression performance.

The bandwidth decomposition can use recursive wavelet transform. The sensed data are multiplied by a first level transform matrix to obtain the first level bandwidth datum, and the first level bandwidth datum is multiplied by a second level transform matrix to obtain the second level bandwidth datum, and so on. The first bandwidth datum to the eleventh bandwidth datum can be obtained. While using the recursive wavelet transform to proceed with bandwidth decomposition, the decimal part of each bandwidth datum is not deleted, each bandwidth datum has large bits. After sequentially obtaining each bandwidth datum, such that the bits of the bandwidth data accumulate to a huge amount. If the decimal part of each bandwidth datum is deleted during the recursive wavelet transform, deletion of the bandwidth data causes an error amount. After sequentially obtaining bandwidth datum, the error amount is amplified continuously, resulting in difficulties in controlling the compression quality of the electrocardiogram.

In an embodiment of the present invention, the bandwidth data includes a first bandwidth datum and a second bandwidth datum. Data of a filter matrix are written into the processor. The first electrocardiogram compressing program is executable by the processor to multiply the sensed data by the filter matrix to obtain the first level bandwidth datum and the second level bandwidth datum. The product of the sensed data and the filter matrix is not limited to simultaneously obtain the first bandwidth datum and the second bandwidth datum. For example, the product of the sensed data and the filter matrix can simultaneously obtain the first to eleventh bandwidth data.

In the present invention, the conventional recursive wavelet transform is used as a basis to integrate the transform matrix of each level required by the bandwidth data into a filter matrix. Thus, the present invention also uses a non-recursive wavelet transform. Specifically, a filter matrix program is written into the processor 22 and can be used by the processor 22 to obtain the filter matrix based on the product of a first level transform matrix and a second level transform matrix. For example, the first level transform matrix can be as follows:

$$\begin{vmatrix} 1 & 0 & 0 & 0 & 1 & 0 & 0 & 0 \\ 1 & 0 & 0 & 0 & -1 & 0 & 0 & 0 \\ 0 & 1 & 0 & 0 & 0 & 1 & 0 & 0 \\ 0 & 1 & 0 & 0 & 0 & -1 & 0 & 0 \\ 0 & 0 & 1 & 0 & 0 & 0 & 1 & 0 \\ 0 & 0 & 1 & 0 & 0 & 0 & -1 & 0 \\ 0 & 0 & 0 & 1 & 0 & 0 & 0 & 1 \\ 0 & 0 & 0 & 1 & 0 & 0 & 0 & -1 \end{vmatrix}$$

The second level transform matrix can be as follows:

$$\begin{vmatrix} 1 & 0 & 1 & 0 \\ 1 & 0 & -1 & 0 \\ 0 & 1 & 0 & 1 \\ 0 & 1 & 0 & -1 \end{vmatrix}$$

To obtain the first level bandwidth datum and the second level bandwidth datum, the processor 22 picks up a low frequency matrix in the first level transform matrix and a high frequency matrix in the second level transform matrix. The low frequency matrix in the first level transform matrix is as follows:

$$\begin{vmatrix} 1 & 0 & 0 & 0 \\ 1 & 0 & 0 & 0 \\ 0 & 1 & 0 & 0 \\ 0 & 1 & 0 & 0 \\ 0 & 0 & 1 & 0 \\ 0 & 0 & 1 & 0 \\ 0 & 0 & 0 & 1 \\ 0 & 0 & 0 & 1 \end{vmatrix}$$

The high frequency matrix in the second level transform matrix is as follows:

$$\begin{vmatrix} 1 & 0 \\ -1 & 0 \\ 0 & 1 \\ 0 & -1 \end{vmatrix}$$

The filter matrix is obtained by multiplying the low frequency matrix and the high frequency matrix. The first bandwidth datum and the second bandwidth datum are obtained after multiplying the sensed data by the filter matrix. Likewise, if it is desired to obtain the first to eleventh bandwidth datum or the bandwidth datum of any level, the above approach can be used to obtain the filter matrix, and the sensed data is multiplied by the filter matrix.

Thus, in comparison with the recursive wavelet transform, each bandwidth datum in the above embodiment has fewer bits to reduce the overall distortion after quantization of each bandwidth datum. Furthermore, the operation amount of the processor 22 is reduced to increase the efficiency and to save electricity.

The second electrocardiogram compressing program is executable by the processor 22 to proceed with quantization and error control. a plurality of quantization scales is used to proceed with quantization of the bandwidth data respectively to obtain a plurality of quantized results. The integer part of each quantized result is set as a quantized datum. The decimal portion of each quantized result is set as a truncated error datum. Each quantization scale is multiplied by a corresponding truncated error datum to obtain a product, and a distortion value is obtained by adding the products.

When the distortion value is not larger than the distortion default value or fulfills a distortion default value range, the processor 22 executes the third electrocardiogram compressing program. On the other hand, when the distortion value is larger than the distortion default value or does not fulfill the distortion default value range, the processor 22 changes a value represented by each quantization scale and re-executes the second electrocardiogram compressing program.

Each bandwidth datum corresponds to a quantization scale. For example, the first bandwidth datum corresponds to a first level quantization scale, the second bandwidth datum corresponds to a second level quantization scale, and so on. When the processor 22 executes the second electrocardiogram compressing program and changes the value represented by each quantization scale for the purposes to make the distortion value not larger than the distortion default value or fulfill the distortion default value range, the processor 22 has to spend plenty of time to continuously change the value represented by each quantization scale. To solve this drawback, a quantization scale program is written into the processor 22. Each quantization scale corresponds to a quadratic equation with one unknown. A quantization scale factor is selected to obtain the quantization scales by using each quadratic equation with one unknown.

For example, the relationships between the first level quantization scale $Q_1$, the second level quantization scale $Q_2$, and the quantization scale factor $Q_F$ are as follows:

$Q_1 = A_1 Q_F^2 + B_1 Q_F - C_1$, and $Q_2 = A_2 Q_F^2 - B_2 Q_F - C_2$ wherein A1, A2, B1, B2, C1, and C2 are coefficients.

Thus, the processor 22 can use a quantization scale to obtain the first level quantization scale and the second level quantization scale. The other level quantization scales can be obtained similarly. Thus, when the distortion value is larger than the distortion default value or does not fulfill the distortion default value range, the processor 22 can simply change the value of the quantization scale factor to obtain the quantization scale of each level. Thus, the processor 22 have a better processing efficiency while changing each quantization scale.

The third electrocardiogram compressing program is executable by the processor 22 to encode the quantized data to obtain the compressed electrocardiogram data. The compressed electrocardiogram data are sent to the data storage unit for storage.

The present invention includes several advantages:

(1) Easy use

The volume of the host 2 makes it portable by a patient. Namely, the electrocardiogram of the patient can be obtained anytime and anywhere without staying in the hospital.

(2) Short Compression Time

The integer arithmetic operation is used when executing the second electrocardiogram compressing program to proceed with quantization and error control to obtain the quantization scales and the truncated error data. The quantization scales and the truncated error data undergo the PRD test while the second electrocardiogram compressing program is proceeding with encoding.

Figure 3:
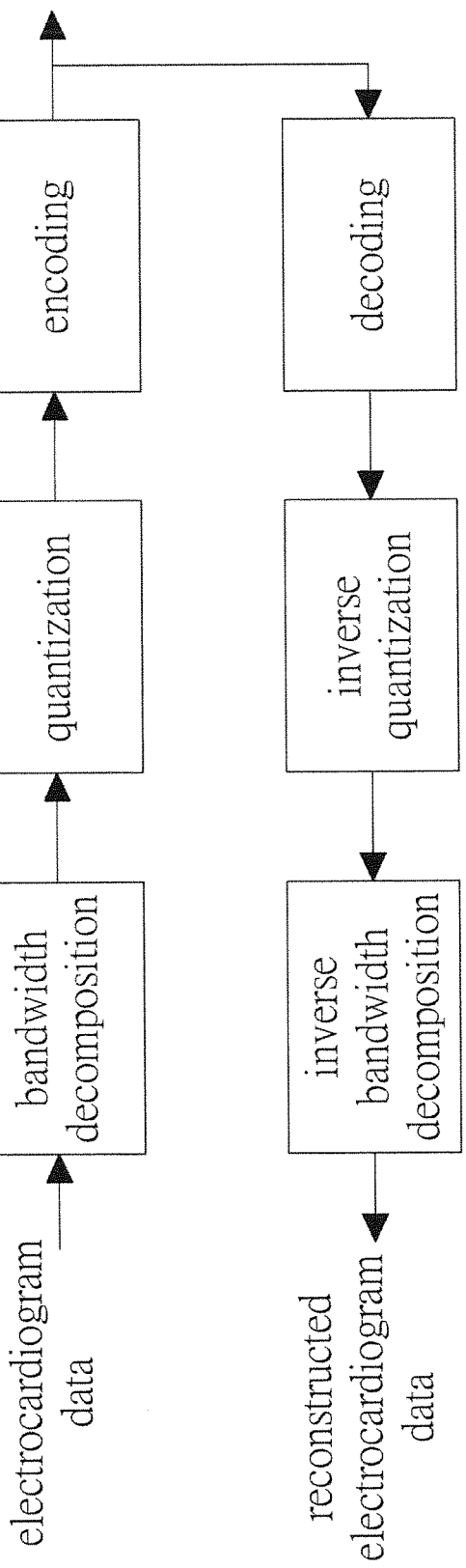
FIG. 3 is a diagrammatic block diagram illustrating a conventional method for compressing electrocardiogram data.

Each quantization scale is multiplied by a corresponding truncated error datum to obtain a product, and the distortion value is obtained by adding the products. The distortion value is examined to identify whether the distortion value fulfills the distortion default value, assuring the compressed electrocardiogram data have a better PRD. This step can be referred to as the PRD mechanism. Thus, the present invention only has to proceed with bandwidth decomposition, quantization, error control, and encoding to obtain the electrocardiogram compressed data. In comparison with the conventional method for compressing the electrocardiogram (FIG. 3) utilizing float point operation that further requires inverse bandwidth decomposition, inverse quantization, and decoding analysis, half time is saved by the present invention. Thus, the processor 22 of the present invention has a low burden and operates at fast speed, saving the energy.

(3) Only one quantization scale factor is sufficient to obtain the quantization scales for proceeding with the error control.

In the conventional error control, the quantization scales are adjusted independently, such that each bandwidth has an independent quantization scale. When adjustment of the quantized result of each bandwidth is desired, each quantization scale must be modulated, such that the whole error control is complicated and less efficient. By contrast, the present invention utilizes only one quantization scale factor to obtain the quantization scales. Thus, the processor 22 has better processing efficiency in changing each quantization scale. Furthermore, the non-recursive wavelet transform is used as a basis when the first electrocardiogram compressing program is executed in the present invention, such that the PRD and the quantization scales are in a linear relationship. Thus, the quantization scales can rapidly be adjusted to fulfil the setting of the PRD while proceeding with error control, increasing the overall operating efficiency.

To permit the doctor to immediately know the heart activity status of the patient, the host 2 can further include an antenna unit 23. The antenna unit 23 permits the compressed electrocardiogram data to be transmitted to a cloud server.

With reference to FIG. 1, a method for compressing an electrocardiogram according to the present invention includes:

(A) proceeding with bandwidth decomposition of electrocardiogram data to obtain a plurality of bandwidth data;

(B) using a plurality of quantization scales to proceed with respective quantization of the plurality of bandwidth data to obtain a plurality of quantized results, with an integer part of each of the plurality of quantized results being set as a quantized datum, with a decimal portion of each of the plurality of quantized results being set as a truncated error datum, and proceeding with an error control in which each of the plurality of quantization scales is multiplied by a corresponding truncated error datum to obtain a product, and a distortion value is obtained by adding the products, wherein when the distortion value is not larger than the distortion default value or fulfills a distortion default value range, a step (C) is executed, wherein when the distortion value is larger than the distortion default value or does not fulfill the distortion default value range, a value represented by each of plurality of quantization scales is changed, and the step (B) is re-executed; and encoding the quantized data to obtain compressed electrocardiogram data.

In step (A), the plurality of bandwidth data includes a first level bandwidth datum and a second level bandwidth datum, and the electrocardiogram data is multiplied by a filter matrix to obtain the first level bandwidth datum and the second level bandwidth datum.

In step (B), each of the plurality of quantization scales corresponds to a quadratic equation with one unknown, and a quantization scale factor is selected to obtain the plurality of quantization scales by using each quadratic equation with one unknown.

The advantages, features, and implantation of the method for compressing an electrocardiogram according to the present invention are substantially the same as those set forth in the above in connection with the wearable electrocardiogram measurement device according to the present invention.

Although specific embodiments have been illustrated and described, numerous modifications and variations are still possible without departing from the scope of the invention. The scope of the invention is limited by the accompanying claims.

The invention claimed is:

1. A wearable electrocardiogram measurement device comprising:

a heart detection unit adapted to be mounted to a skin of a human body for detecting an activity status of a heart of the human body to obtain electrocardiogram data; and a host portable by a user, with the host including a data storage unit and a processor, with the data storage unit configured to store compressed electrocardiogram data, with the processor electrically connected to the heart detection unit and the data storage unit, and with first, second, and third electrocardiogram compressing programs and a distortion default value being written into the processor, with the first electrocardiogram compressing program executable by the processor to proceed with bandwidth decomposition of sensed data obtained from the heart detection unit, obtaining a plurality of bandwidth data, with the second electrocardiogram compressing program executable by the processor to proceed with quantization of the plurality of bandwidth data respectively by using a plurality of quantization scales to obtain a plurality of quantized results, with an integer part of each of the plurality of quantized results being set as a quantized datum, with a decimal portion of each of the plurality of quantized results being set as a truncated error datum, with each of the plurality of quantization scales multiplied by a corresponding truncated error datum to obtain a product, and with a distortion value obtained by adding the products, wherein when the distortion value is not larger than the distortion default value or fulfills a distortion default value range, the third electrocardiogram compressing program is executed, wherein when the distortion value is larger than the distortion default value or does not fulfill the distortion default value range, a value represented by each of plurality of quantization scales is changed, and the second electrocardiogram compressing program is re-executed, and wherein the third electrocardiogram compressing program is executable by the processor to encode the quantized data to obtain the compressed electrocardiogram data, and the compressed electrocardiogram data are sent to the data storage unit for storage.

2. The wearable electrocardiogram measurement device as claimed in claim 1, with the plurality of bandwidth data including a first level bandwidth datum and a second level bandwidth datum, with data of a filter matrix written into the processor, with the first electrocardiogram compressing program executable by the processor to multiply the sensed data by the filter matrix to obtain the first level bandwidth datum and the second level bandwidth datum.

3. The wearable electrocardiogram measurement device as claimed in claim 2, with a quantization scale program being written into the processor, with the quantization scale program executable by the processor, wherein each of the plurality of quantization scales corresponds to a quadratic equation with one unknown, and wherein a quantization scale factor is selected to obtain the plurality of quantization scales by using each quadratic equation with one unknown.

4. The wearable electrocardiogram measurement device as claimed in claim 1, with the host further including an antenna unit, and with the antenna unit permitting transmission of the compressed electrocardiogram data to a cloud server.

5. A method for compressing an electrocardiogram, comprising:
(A) proceeding with bandwidth decomposition of electrocardiogram data to obtain a plurality of bandwidth data;
(B) using a plurality of quantization scales to proceed with respective quantization of the plurality of bandwidth data to obtain a plurality of quantized results, with an integer part of each of the plurality of quantized results being set as a quantized datum, with a decimal portion of each of the plurality of quantized results being set as a truncated error datum, and proceeding with an error control in which each of the plurality of quantization scales is multiplied by a corresponding truncated error datum to obtain a product, and a distortion value is obtained by adding the products, wherein when the distortion value is not larger than the distortion default value or fulfills a distortion default value range, a step (C) is executed, wherein when the distortion value is larger than the distortion default value or does not fulfill the distortion default value range, a value represented by each of plurality of quantization scales is changed, and the step (B) is re-executed; and
encoding the quantized data to obtain compressed electrocardiogram data.

6. The method for compressing an electrocardiogram as claimed in claim 5, wherein in the step (A), the plurality of bandwidth data includes a first level bandwidth datum and a second level bandwidth datum, and the electrocardiogram data is multiplied by a filter matrix to obtain the first level bandwidth datum and the second level bandwidth datum.

7. The method for compressing an electrocardiogram as claimed in claim 6, wherein in the step (B), each of the plurality of quantization scales corresponds to a quadratic equation with one unknown, and a quantization scale factor is selected to obtain the plurality of quantization scales by using each quadratic equation with one unknown.

* * * * *